US00PP33130P3

(12) United States Plant Patent
Klemm et al.

(10) Patent No.: US PP33,130 P3
(45) Date of Patent: Jun. 1, 2021

(54) ***CALIBRACHOA* PLANT NAMED 'KLECA18501'**

(50) Latin Name: ***Calibrachoa* sp.**
Varietal Denomination: KLECA18501

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/871,010

(22) Filed: May 10, 2020

(65) Prior Publication Data

US 2020/0383257 P1 Dec. 3, 2020

Related U.S. Application Data

(60) Provisional application No. 62/921,069, filed on May 29, 2019.

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 6/821; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Calibrachoa* plant designated 'KLECA18501' particularly distinguished by vivid orange-red flowers, is disclosed.

1 Drawing Sheet

Genus and species: *Calibrachoa* sp.
Variety denomination: 'KLECA18501'.

BACKGROUND OF THE NEW PLANT

The present invention comprises a new and distinct variety of *Calibrachoa*, botanically known as *Calibrachoa* sp., and hereinafter referred to by the variety name 'KLECA18501'. 'KLECA18501' originated from a controlled cross between the proprietary female *Calibrachoa* parent 'CA-2015-6360', (unpatented) and the proprietary male *Calibrachoa* 'CA-2015-6416', (unpatented) in Stuttgart, Germany in August 2015.

'KLECA18501' has been found to reproduce true to type in successive generations of asexual propagation in Stuttgart, Germany via vegetative stem cuttings.

SUMMARY

The following are the most outstanding and distinguishing characteristics of 'KLECA18501' when grown under normal horticultural practices in Stuttgart, Germany.

1. Vivid orange-red flowers; and
2. A semi-upright habit.

DESCRIPTION OF THE PHOTOGRAPH

This new *Calibrachoa* plant is illustrated by the accompanying photograph of a plant grown outdoors in Stuttgart, Germany. The photograph shows the whole plant, unless otherwise noted, including the flowers and foliage and buds. The colors shown are as true as can be reasonably obtained by conventional photographic procedures. The photograph is of a whole plant photo of 'KLECA18501', 10-weeks-old, taken in April 2017.

DESCRIPTION OF THE NEW VARIETY

The following detailed descriptions set forth the distinctive characteristics of 'KLECA18501'. The data which define these characteristics were collected from asexual reproductions carried out in Stuttgart, Germany. Data was collected on plants grown 18 weeks since potting in a greenhouse with no pinching or growth regulators. Color references are to The R.H.S. Colour Chart of The Royal Horticultural Society of London (R.H.S.), 5$^{th}$ edition (2007).

Classification:
*Family.*—Solanaceae.
*Botanical.*—*Calibrachoa* sp.
*Designation.*—'KLECA18501'.

Parentage:
*Female parent.*—'CA-2015-6360' (unpatented).
*Male parent.*—'CA-2015-6416' (unpatented).

Plant:
*Life cycle.*—Annual.
*Form.*—Short-lived subshrub.
*Habit.*—Semi-upright.
*Height (from soil line to top of foliage).*—17.5 cm.
*Spread.*—62 cm.
*Propagation.*—Vegetative.
*Type cuttings.*—Tip cuttings.
*Time to produce a rooted cutting.*—3 weeks.

Stems:
*Stem color.*—RHS 144B.
*Pubescence.*—Present.
*Pubescence color.*—RHS 155A.
*Stem diameter.*—0.25 cm.
*Stem length.*—From soil line to first node: 1.8 cm. Total length: 46 cm.
*Internode length.*—1.5 cm.

Foliage:
*Arrangement*.—Alternate.
*Shape*.—Lanceolate.
*Apex*.—Broadly acute.
*Base*.—Attenuate.
*Margin*.—Ciliate.
*Surface*.—Moderately glandular pubescent.
*Surface pubescence*.—Present.
*Pubescence color*.—RHS 155A.
*Venation*.—Arcuate.
*Venation color*.—Upper surface: RHS 143C. Lower surface: RHS 145B.
*Length*.—3.2 cm to 4.4 cm.
*Width*.—1.1 cm to 1.7 cm.
*Variegation*.—Absent.
*Color*.—Upper surface: RHS 137B. Lower surface: RHS 147B.
*Fragrance*.—Absent.

Inflorescence:
*Flowering habit*.—Single flowers.
*Flower type*.—Determinate inflorescence.
*Flowering requirements*.—A minimum of light sun is required.
*Duration of flowers*.—6 days.
*Corolla surface texture*.—Smooth.
*Shape*.—Funnel form.
*Fragrance*.—Absent.
*Lobing of the flower*.—Medium.
*Conspicuousness of the veins of the flower*.—Weak.
*Flower depth*.—2.8 cm.
*Flower tube length*.—1.2 cm.
*Flower tube diameter*.—0.7 cm.
*Flower diameter*.—3.2 cm.
*Pedicel color*.—RHS 143C.
*Pedicel length*.—1.5 cm to 2.7 cm.
*Calyx*.—Funnel shaped when bud closed, star shaped when flower open.

Inflorescence bud:
*Surface*.—Smooth.
*Length*.—2.1 cm.
*Diameter*.—0.3 cm.
*Shape*.—Elliptic.
*Color*.—RHS 154C (throat) and RHS 33D (limb).

Peduncles:
*Length*.—1.5 cm to 2.7 cm.
*Diameter*.—0.1 cm.
*Color*.—RHS 143C.
*Texture*.—Puberulent.
*Anthocyanin color*.—Absent.

Sepals:
*Shape*.—Lanceolate.
*Apex*.—Narrowly acute.
*Margin*.—Ciliate.
*Length*.—1.7 cm.
*Diameter*.—0.3 cm.
*Sepal color*.—Upper surface: RHS 137C. Lower surface: RHS 138B.

Petals:
*Shape*.—Obcordate.
*Length*.—1.5 cm.
*Apex*.—Truncate.
*Margin*.—Entire.
*Base*.—Fused in the tube.
*Texture, upper surface*.—Glabrous.
*Texture, lower surface*.—Glandular pubescent, dense along venation.
*Lobe length*.—0.7 cm.
*Lobe width*.—1.6 cm.
*Color*.—Lobe color: Upper surface: RHS 33B. Lower surface: RHS 33D. Corolla tube color: Inner: RHS 5C. Outer: RHS 4C.
*Fragrance*.—Absent.

Reproductive organs:
*Stamen number*.—5.
*Anther color*.—RHS 4A.
*Filament color*.—RHS 2C.
*Pollen color*.—RHS 8B.
*Pollen amount*.—Moderate.
*Placenta arrangement*.—Ovate.
*Pistil number*.—1.
*Pistil length*.—0.9 cm.
*Stigma color*.—RHS 149A.
*Style length*.—0.85 cm.
*Style color*.—RHS 149C.

Fruit and seed set: No fruit or seed set observed.

COMPARISON OF 'KLECA18501' WITH PARENTAL LINES AND KNOWN VARIETY

'KLECA18501' is distinguished from the parental lines as follows. Whereas 'KLECA18501' has a vivid orange-red main lobe color, the female parent 'CA-2015-6360' has a yellow with red veins and red transition to corolla tube color and the male parent 'CA-2015-6416' has yellow with a red transition to corolla tube color.

'KLECA18501' can be compared to the commercial *Calibrachoa* variety COLIBRI 'Orange' (patent status unknown) as follows. 'KLECA18501' flowers earlier and is more vigorous than COLIBRI 'Orange'. Additionally, 'KLECA18501' is resistant to mildew, *Podosphaera xanthii*, whereas COLIBRI 'Orange' has low susceptibility.

We claim:

1. A new and distinct variety of *Calibrachoa* plant designated 'KLECA18501' as illustrated and described herein.

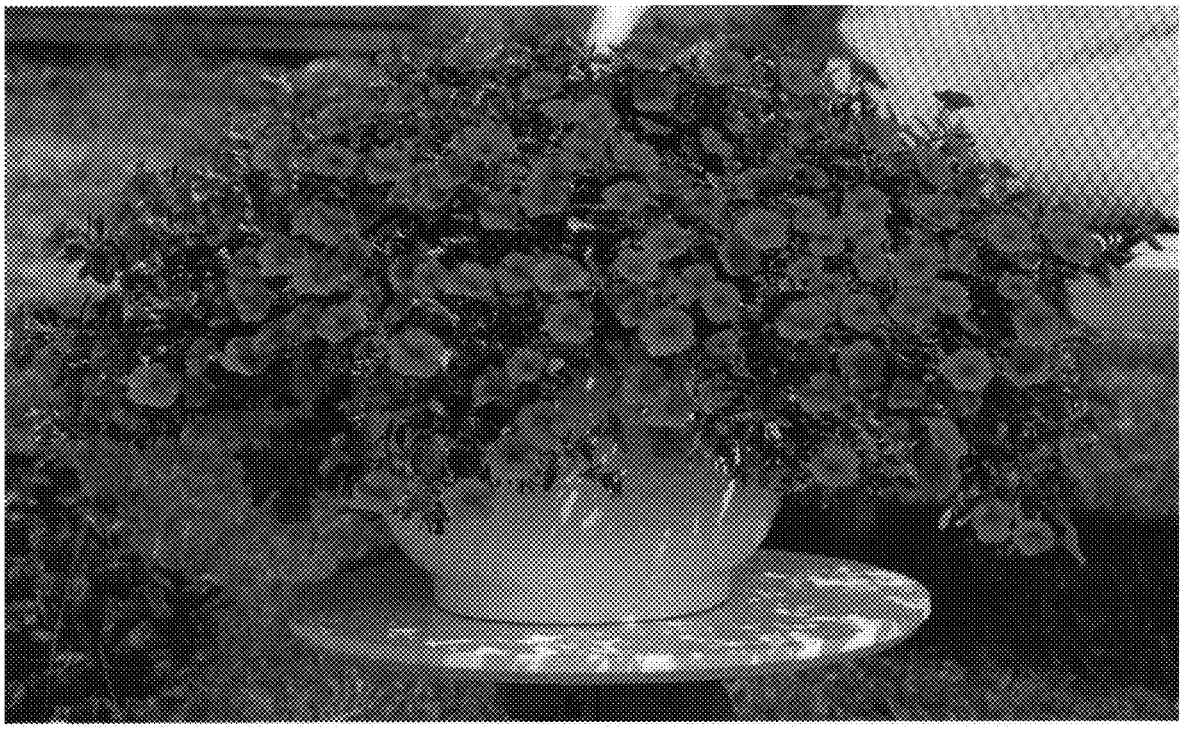

* * * * *